(12) United States Patent
Takeuchi et al.

(10) Patent No.: US 9,867,920 B2
(45) Date of Patent: Jan. 16, 2018

(54) MEDICAL INSTRUMENT

(71) Applicant: Terumo Kabushiki Kaisha, Shibuya-ku (JP)

(72) Inventors: Kazuhiko Takeuchi, Fujinomiya (JP); Eisuke Sasaki, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 367 days.

(21) Appl. No.: 14/495,269

(22) Filed: Sep. 24, 2014

(65) Prior Publication Data

US 2015/0010434 A1 Jan. 8, 2015

Related U.S. Application Data

(63) Continuation of application No. PCT/JP2013/057078, filed on Mar. 13, 2013.

(30) Foreign Application Priority Data

Mar. 26, 2012 (JP) ................. 2012-070140

(51) Int. Cl.
*A61M 1/16* (2006.01)
*B01D 63/02* (2006.01)
*B65H 81/00* (2006.01)

(52) U.S. Cl.
CPC ........ *A61M 1/1698* (2013.01); *A61M 1/1623* (2014.02); *B01D 63/021* (2013.01);
(Continued)

(58) Field of Classification Search
CPC . A61M 1/1698; B01D 63/021; B01D 63/025; B01D 2313/38; B01D 2323/42;
(Continued)

(56) References Cited

U.S. PATENT DOCUMENTS 4,210,536 A 7/1980 Coplan et al.
5,346,621 A * 9/1994 Haworth ................ B01D 63/02
210/645

(Continued)

FOREIGN PATENT DOCUMENTS

EP 0 372 146 A1 6/1990
EP 0 798 034 A1 10/1997
(Continued)

OTHER PUBLICATIONS

The extended European Search Report dated Nov. 30, 2015, by the European Patent Office in corresponding European Patent Application No. 13768804.0-1651. (7 pages).
(Continued)

*Primary Examiner* — Tatyana Zalukaeva
*Assistant Examiner* — Benjamin Klein
(74) *Attorney, Agent, or Firm* — Buchanan Ingersoll & Rooney PC

(57) ABSTRACT

An Oxygenator as a medical instrument includes at least one first hollow fiber membrane layer comprised of a plurality of integrated first hollow fiber membranes, and forms a shape of a cylindrical body as a whole, and at least one second hollow fiber membrane layer disposed at the outer circumferential side of the first hollow fiber membrane layer in a state of being concentric with the first hollow fiber membrane layer, has a plurality of integrated second hollow fiber membranes, and forms a shape of a cylindrical body as a whole. Moreover, each of the first hollow fiber membranes is wound around a central axis, and each of the second hollow fiber membranes is wound around a central axis. The number of times the second hollow fiber membranes are wound is smaller than the number of times the first hollow fiber membranes are wound.

17 Claims, 10 Drawing Sheets

(52) U.S. Cl.
CPC ........... *B01D 63/025* (2013.01); *B65H 81/00* (2013.01); *B01D 2313/38* (2013.01); *F04C 2270/041* (2013.01)

(58) Field of Classification Search
CPC ..... B65H 81/02; F28D 7/103; F28D 21/0015; F28D 2021/005
See application file for complete search history.

(56) References Cited

U.S. PATENT DOCUMENTS

| | | | | |
|---|---|---|---|---|
| 5,376,334 | A | * | 12/1994 | Haworth ................ B01D 63/02 210/321.87 |
| 6,503,451 | B2 | | 1/2003 | Ikeda et al. |
| 6,824,679 | B1 | | 11/2004 | Dzengeleski et al. |
| 2002/0039543 | A1 | | 4/2002 | Ikeda et al. |

FOREIGN PATENT DOCUMENTS

| | | |
|---|---|---|
| EP | 1 108 462 A2 | 6/2001 |
| JP | 1-33206 B2 | 7/1989 |
| JP | 7-509171 A | 10/1995 |
| JP | 2001-170168 A | 6/2001 |
| JP | 2001-178818 A | 7/2001 |
| JP | 2002-532220 A | 10/2002 |
| WO | 00/35567 A1 | 6/2000 |

OTHER PUBLICATIONS

International Search Report (PCT/ISA/210) dated Jun. 18, 2013, by the Japanese Patent Office as the International Searching Authority for International Application No. PCT/JP2013/057078.
European Patent Office Action dated Oct. 4, 2017 in corresponding European Application No. 13768804.0 (4 pages total)

* cited by examiner

MEDICAL INSTRUMENT

CROSS-REFERENCES TO RELATED APPLICATIONS

This application is a continuation of International Application No. PCT/JP2013/057078 filed on Mar. 13, 2013, and claims priority to Japanese Application No. 2012-070140 filed on Mar. 26, 2012, the entire content of both of which is incorporated herein by reference.

TECHNICAL FIELD

The present invention relates to a medical instrument.

BACKGROUND DISCUSSION

In the related art, an Oxygenator which performs gas exchange using a hollow fiber membrane layer constituted with a plurality of hollow fiber membranes is known (for example, see U.S. Pat. No. 6,503,451).

The Oxygenator described in U.S. Pat. No. 6,503,451 has a housing, hollow fiber membrane layers which are housed in the housing and form a cylindrical shape as a whole, a blood inlet, a blood outlet, a gas inlet, and a gas outlet. In the Oxygenator, through each hollow fiber membrane, gas exchange between blood and gas, (i.e., a process of adding oxygen and removing carbon dioxide) occurs.

In the hollow fiber membrane layers having a shape of a cylindrical body, a plurality of hollow fiber membranes are integrated and laminated on one another. In each of the layers, hollow fiber membranes are wound one by one around the central axis of the cylindrical body, and in this state, the hollow fiber membranes travel between a partition at one end of the cylindrical body and a partition at the other end of the cylindrical body. In an outward path heading for the partition at the other end from the partition at one end, each hollow fiber membrane is wound at least once around the central axis of the cylindrical body. Moreover, in a homeward path heading for the partition at one end from the partition at the other end, each hollow fiber membrane is also wound at least once around the central axis of the cylindrical body.

In each of the hollow fiber membranes wound as above, a length of the layer wound once around the central axis of the cylindrical body increases toward the outer circumference of the cylindrical hollow fiber membrane layer. The Oxygenator has a problem in that the larger the length of the hollow fiber membrane from one partition to the other partition is, the greater the pressure loss of gas passing through the inside of the hollow fiber membrane becomes.

SUMMARY

The present applications provides a medical instrument in which a length of each of the first hollow fiber membrane and second hollow fiber membrane from one partition to the other partition does not exceed a certain length.

A medical instrument includes at least one first hollow fiber membrane layer comprised of a plurality of integrated first hollow fiber membranes, and configured as a cylindrically-shaped body, and at least one second hollow fiber membrane layer disposed at the outer circumferential side of the first hollow fiber membrane layer concentric with the first hollow fiber membrane layer, the second hollow fiber membrane having a plurality of integrated second hollow fiber membranes, and configured as a cylindrically-shaped body, in which each of the first hollow fiber membranes and the second hollow fiber membranes is wound around the central axis of the cylindrical body, and a total number of times the second hollow fiber membranes are wound is smaller than a total number of times the first hollow fiber membranes are wound.

The medical instrument can be configured so that each of the first hollow fiber membranes passes through an outward path heading for the other end from one end of the cylindrical body and a homeward path heading for one end from the other end, is wound at least once around the central axis in the outward path, and is wound at least once around the central axis in the homeward path.

The medical instrument can also be configured so that each of the first hollow fiber membranes sequentially passes through a starting point which is set at one site of one end of the cylindrical body, a midpoint which is set at one site of the other end of the cylindrical body such that the midpoint is placed in the almost same position as the starting point in the circumferential direction of the cylindrical body, and an endpoint which is set at one site which is in the same position as the starting point or is in a position deviating from the starting point around the central axis, is wound at least once along the circumferential direction of the cylindrical body in the outward path heading for the midpoint from the starting point, and is wound at least once along the circumferential direction of the cylindrical body in the same direction as in the case of the outward path in the homeward path heading for the endpoint from the midpoint.

In each of the first hollow fiber membranes, a series of pathways having the outward path and the homeward path are repeated plural times.

(According to one embodiment, each of the second hollow fiber membranes passes through the outward path heading for the other end from one end of the cylindrical body and the homeward path heading for one end from the other end, and is wound once around the central axis while passing through the outward path and the homeward path.

According to another embodiment, each of the second hollow fiber membranes sequentially passes through a starting point which is set at one site of one end of the cylindrical body, a midpoint which is set at one site of the other end of the cylindrical body such that the midpoint is located in a position opposite to the starting point across the central axis of the cylindrical body, and an endpoint which is set at one site which is in the same position as the starting point or is in a position deviating from the starting point around the central axis, reaches the midpoint from the starting point at the shortest distance while being wound along the circumferential direction of the cylindrical body in the outward path heading for the midpoint from the starting point, and reaches the endpoint from the midpoint at the shortest distance while being wound along the circumferential direction of the cylindrical body in the same direction as in the case of the outward path in the homeward path heading for the endpoint from the midpoint.

With the second hollow fiber membrane configured as described above, in each of the second hollow fiber membranes, a series of pathways having the outward path and the homeward path are repeated plural times.

The inner diameter of the first hollow fiber membranes can be the same as the inner diameter of the second hollow fiber membranes.

The outer diameter of the first hollow fiber membranes can be the same as the outer diameter of the second hollow fiber membranes.

It is possible to configure the gap between the first hollow fiber membranes adjacent to each other to be the same as the gap between the second hollow fiber membranes adjacent to each other.

Moreover, the materials constituting the first hollow fiber membranes can be the same as materials constituting the second hollow fiber membranes.

The length of the first hollow fiber membrane layer extending along the central axis direction is preferably the same as a length of the second hollow fiber membrane layer extending along the central axis direction.

The medical instrument can be configured to include a plurality of the first hollow fiber membrane layers and a plurality of the second hollow fiber membrane layers, in which a first laminate is constituted with the plurality of the first hollow fiber membrane layers, and a second laminate is constituted with the plurality of the second hollow fiber membrane layers.

Each of the first hollow membrane layer and the second hollow membrane layer has either a function of performing gas exchange or a function of performing heat exchange.

The medical instrument is preferably an Oxygenator.

The number of times the second hollow fiber membranes, which constitute the second hollow fiber membrane layer positioned at the outer side, that is, the second hollow fiber membrane layer having a larger diameter between the first hollow fiber membrane layer and the second hollow fiber membrane layer, are wound is smaller than the number of times the first hollow fiber membranes, which constitute the first hollow fiber membrane layer having a smaller diameter, are wound. Consequentially, increase in the length of the second hollow fiber membranes from one partition to the other partition is prevented. As a result, it is possible to inhibit pressure loss from occurring in the second hollow fiber membranes when fluid passes through the inside of the second hollow fiber membranes.

Moreover, in the first hollow fiber membrane layer positioned in the inner side, the length of the first hollow fiber membranes from one partition to the other partition is controlled to be within a prescribed length. Accordingly, it is possible to inhibit pressure loss from occurring in the first hollow fiber membranes when fluid passes through the inside of the first hollow fiber membranes.

A production method of a medical instrument is disclosed where the medical instrument includes a first hollow fiber membrane layer comprised of a plurality of integrated first hollow fiber membranes, and a second hollow fiber membrane layer comprised of a plurality of integrated second hollow fiber membranes. The production method comprises configuring the first hollow fiber membrane layer as a cylindrically-shaped body by helically winding each of the first hollow fiber membranes around a central circumferential axis, wherein each helical winding of the first hollow fiber membrane layer traverses a central axis extending along an axial direction of the cylindrically-shaped body a first set number of times, and helically winding each of the second hollow fiber membranes to encircle the first hollow fiber membrane layer, wherein each helical winding of the second hollow fiber membrane layer traverses a central axis a second set number of times different that the first set of number of times.

DETAILED DESCRIPTION

Figure 1:
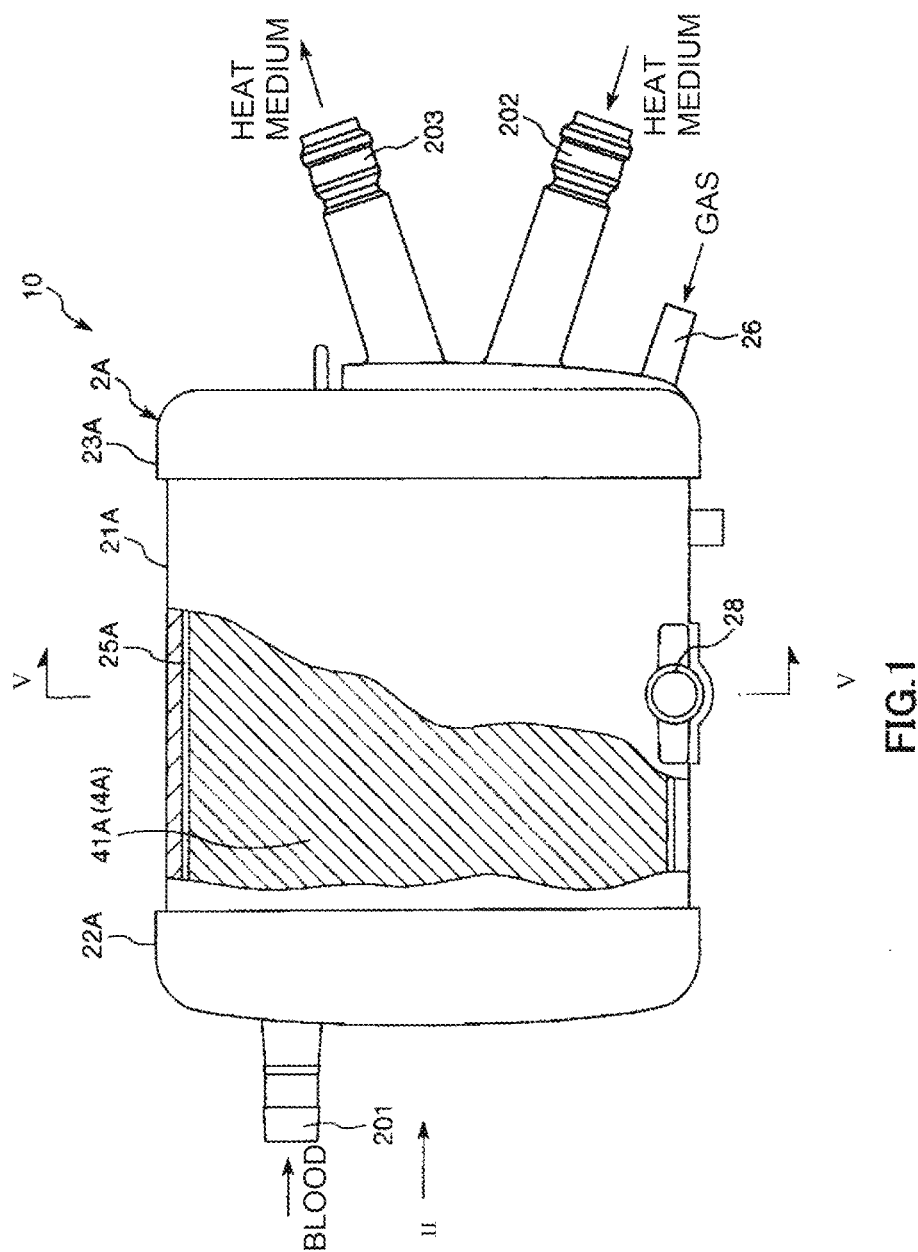
FIG. 1 is a plan view showing an embodiment in a case where the medical instrument is applied to an Oxygenator.
Figure 2:
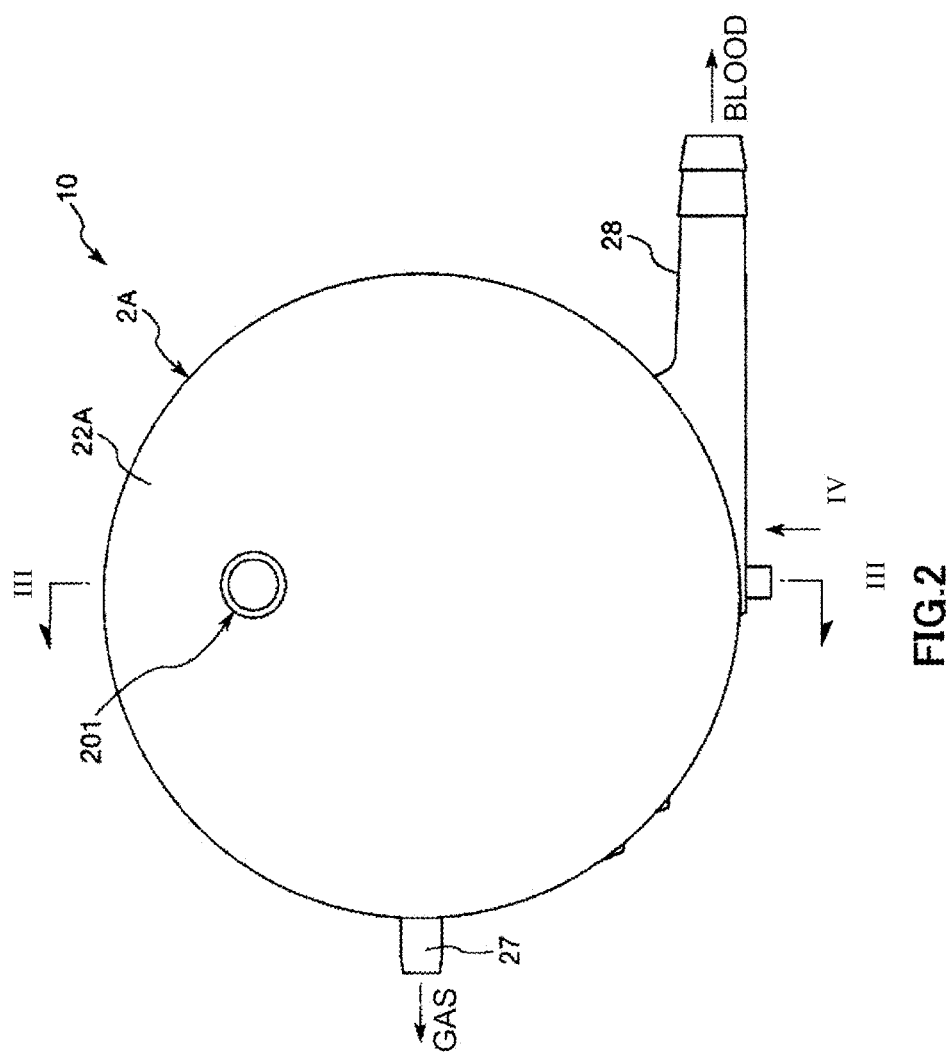
FIG. 2 is a view obtained when the Oxygenator shown in FIG. 1 is viewed from the direction of arrow II.

Hereinafter, the medical instrument will be described in detail, based on preferable embodiments shown in attached drawings.

The left side in FIGS. 1, 3, 4, and 7 to 9 will be described as "left" or "left-hand side", and the right side in the drawings will be described as "right" or "right-hand side". Furthermore, in FIG. 1 to FIG. 7, the inside of the Oxygenator will be described as "blood inlet side" or "upstream side", and the outside of the Oxygenator will be described as "blood outlet side" or "downstream side".

An Oxygenator 10 shown in FIG. 1 to FIG. 5 has a columnar shape. The Oxygenator 10 is an Oxygenator equipped with a heat exchanger that includes a heat exchange portion 10B disposed in the inside and performs heat exchange with blood, and an Oxygenator portion 10A disposed at the outer circumferential side of the heat exchange portion 10B and performs gas exchange with blood. The Oxygenator 10 is installed in an extracorporeal blood circulation circuit.

The Oxygenator 10 has a housing 2A, and the Oxygenator portion 10A and the heat exchange portion 10B are housed in the housing 2A.

The housing 2A is constituted with a cylindrical housing main body 21A, a dish-shaped first cap (left-side cap) 22A that seals a left-end opening of the cylindrical housing main body 21A, and a dish-shaped second cap (right-side cap) 23A that seals a right-end opening of the cylindrical housing main body 21A.

The cylindrical housing main body 21A, the first cap 22A, and the second cap 23A are constituted with a resin material. The first cap 22A and the second cap 23A are fixed to the cylindrical housing main body 21A, by a method such as fusion or bonding utilizing an adhesive.

In the outer circumferential portion of the cylindrical housing main body 21A, a tubular blood outlet port 28 is formed. The blood outlet port 28 protrudes in a direction approximately tangential to the outer circumferential surface of the cylindrical housing main body 21A (see FIG. 5).

A tubular blood inlet port 201 and a gas outlet port 27 protrude from the first cap 22A. The blood inlet port 201 is formed in the end surface of the first cap 22A such that the central axis of the blood inlet port 201 becomes eccentric with respect to the center of the first cap 22A. The gas outlet port 27 is formed in the outer circumferential portion of the first cap 22A such that the central axis of the gas outlet port crosses (i.e., is coaxial with) the center of the first cap 22A (see FIG. 2).

In the second cap 23A, a tubular gas inlet port 26, a heat medium inlet port 202, and a heat medium outlet port 203 are formed in a state of protruding from the second cap 23A. The gas inlet port 26 is formed at the edge of the end surface of the second cap 23A. The heat medium inlet port 202 and the heat medium outlet port 203 are respectively formed in a portion approximately corresponding to the central portion of the end surface of the second cap 23A. Moreover, each of the centerline of the heat medium inlet port 202 and the centerline of the heat medium outlet port 203 is slightly oblique to the centerline of the second cap 23A.

Note that, the housing 2A does not need to form a shape of a complete cylinder as a whole. For example, the housing 2A may form a partially defective shape or form a shape to which a portion having different shape has been added.

Figure 3:
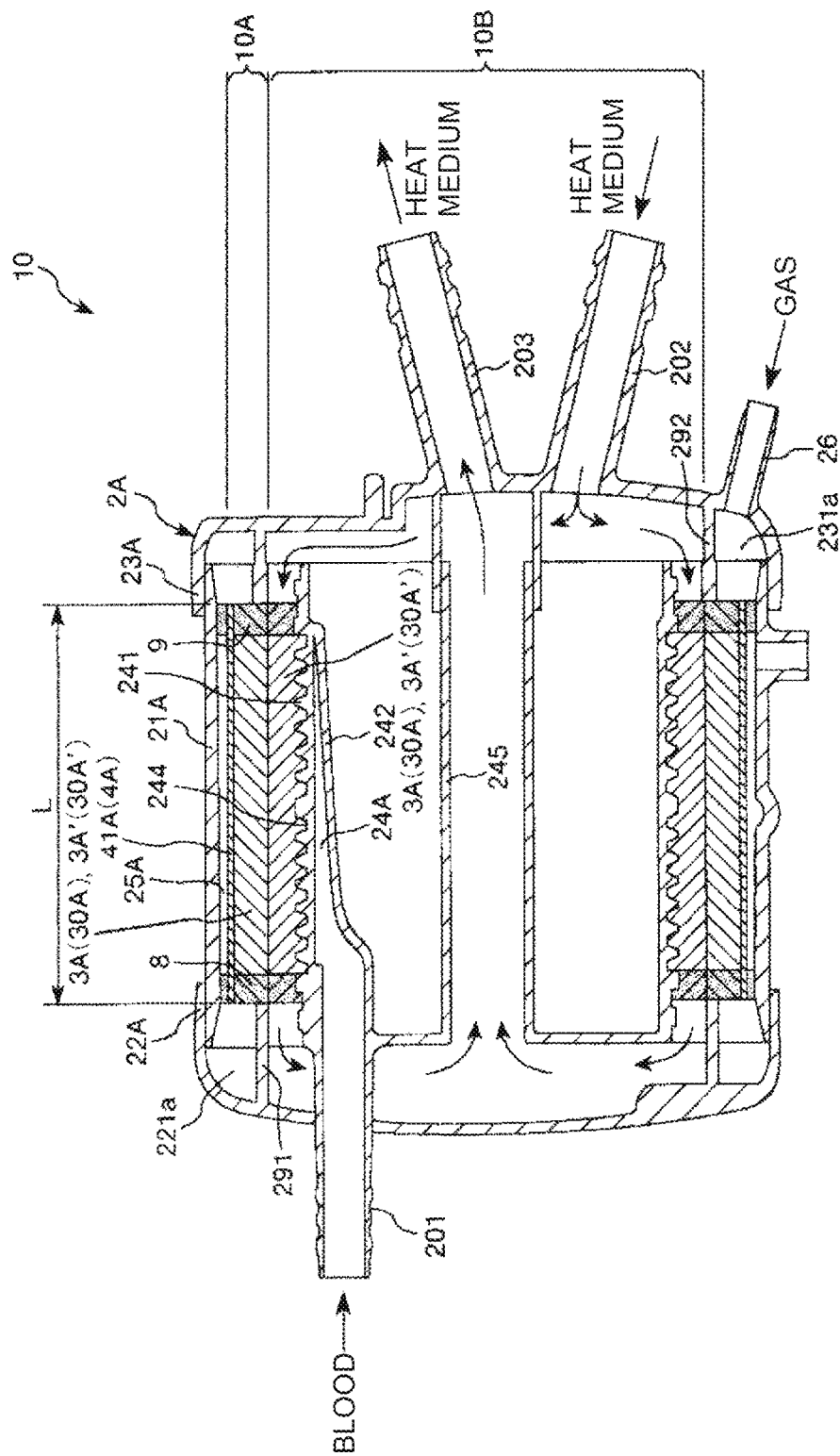
FIG. 3 is a cross-sectional view taken along the section line III-III in FIG. 2.
Figure 4:
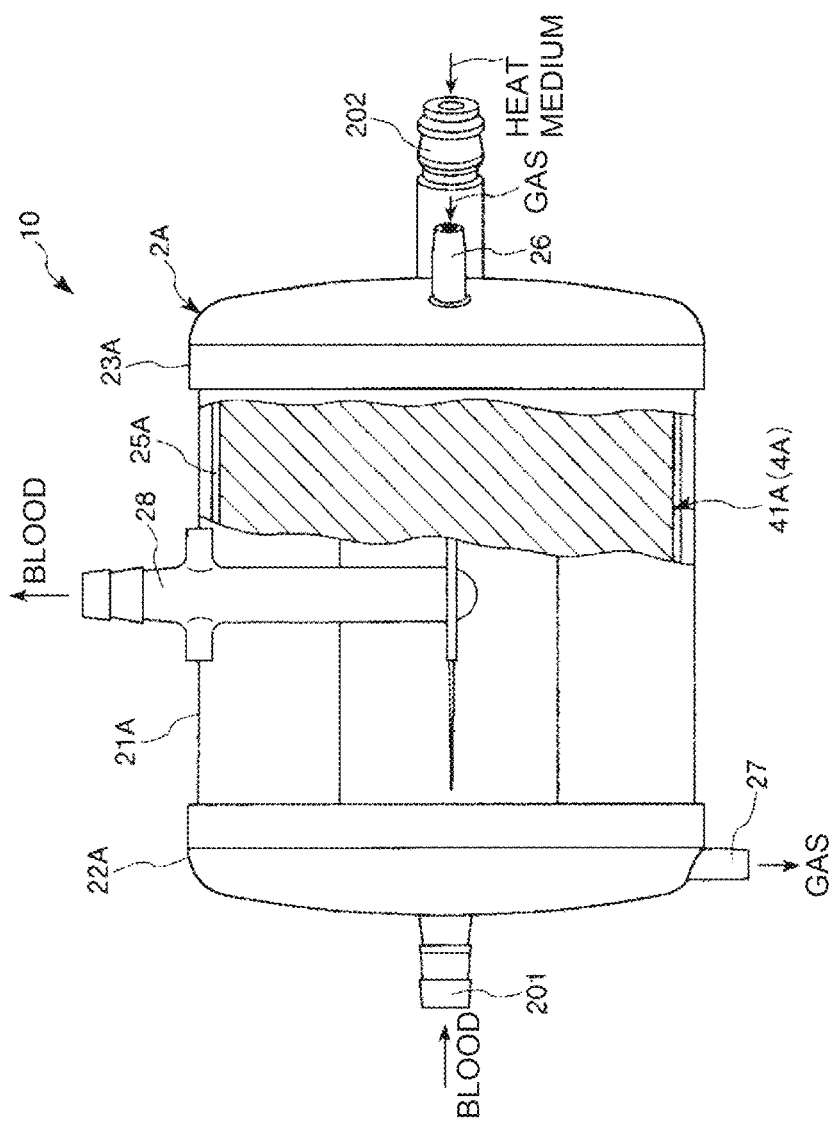
FIG. 4 is a view seen from the direction of arrow IV in FIG. 2.
Figure 5:
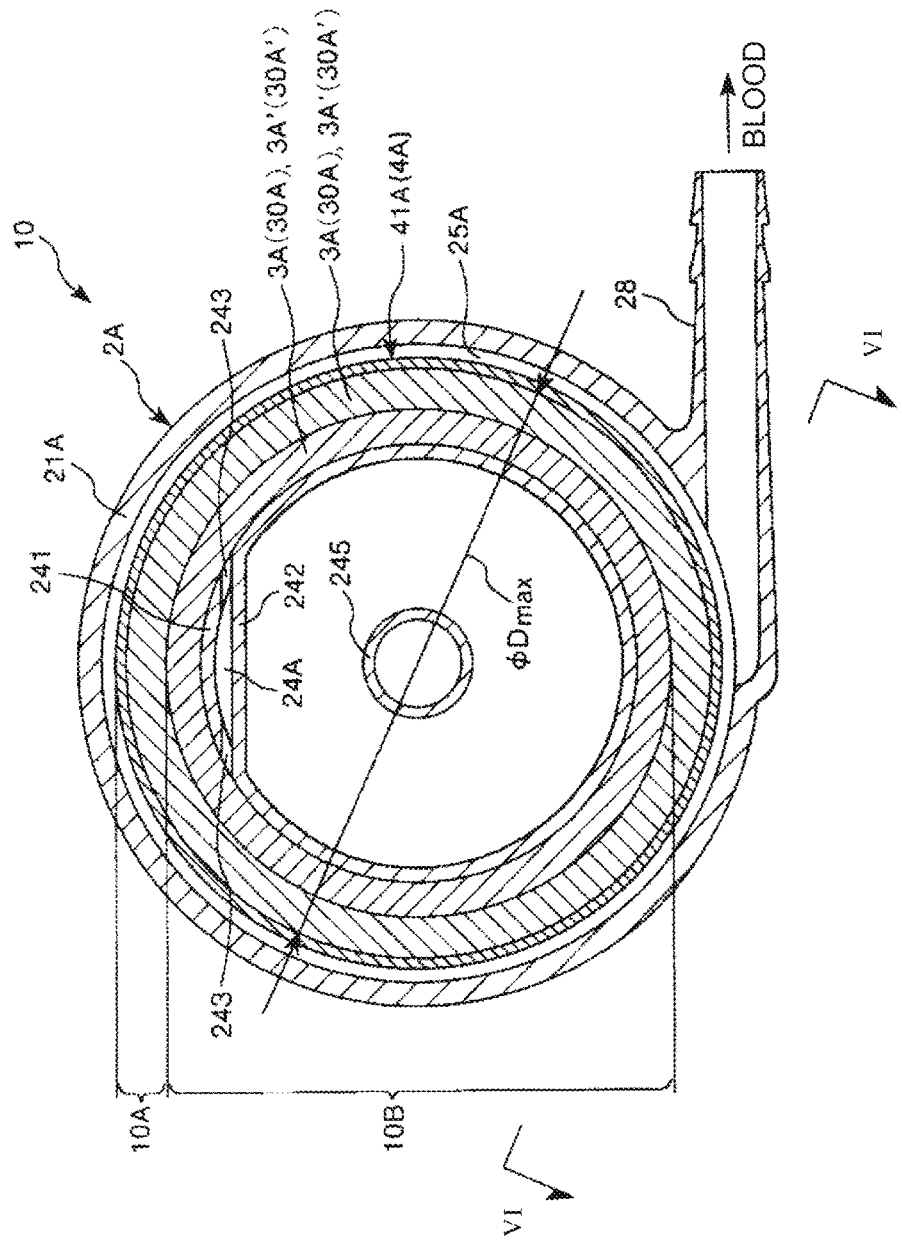
FIG. 5 is a cross-sectional view taken along the section line V-V in FIG. 1.

As shown in FIG. 3 and FIG. 5, the Oxygenator portion 10A, having a cylindrical shape along the inner circumferential surface of the housing 2A, is housed in the housing 2A. The Oxygenator portion 10A is constituted with a first laminate 30A that has a cylindrical body as a whole, a second laminate 30A' that forms a shape of a cylindrical body as a whole, and a filter member 41A as air bubble-removing means 4A.

Figure 7:
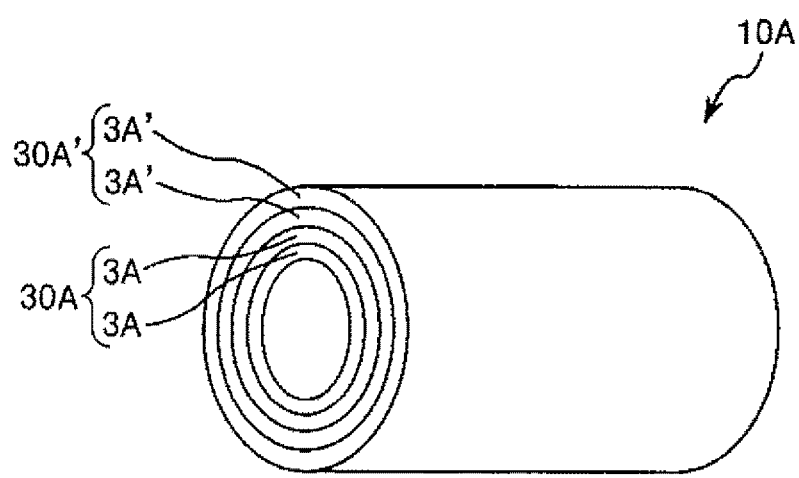
FIG. 7 is a perspective view showing a first hollow fiber membrane layer and a second hollow fiber membrane layer included in the Oxygenator shown in FIG. 1.

As shown in FIG. 7, at the outer circumferential side (blood outlet portion side) of the first laminate 30A (first hollow fiber membrane layer 3A), the second laminate 30A' is disposed in a state of being concentric with the first laminate 30A. That is, the second laminate 30A' surrounds or encircles the first laminate 30A. Moreover, at the outer circumferential side of the second laminate 30A', the filter member 41A is disposed.

The first laminate 30A includes a plurality of first hollow fiber membrane layers 3A. In addition, the second laminate 30A' includes a plurality of second hollow fiber membrane layers 3A'.

Figure 6:
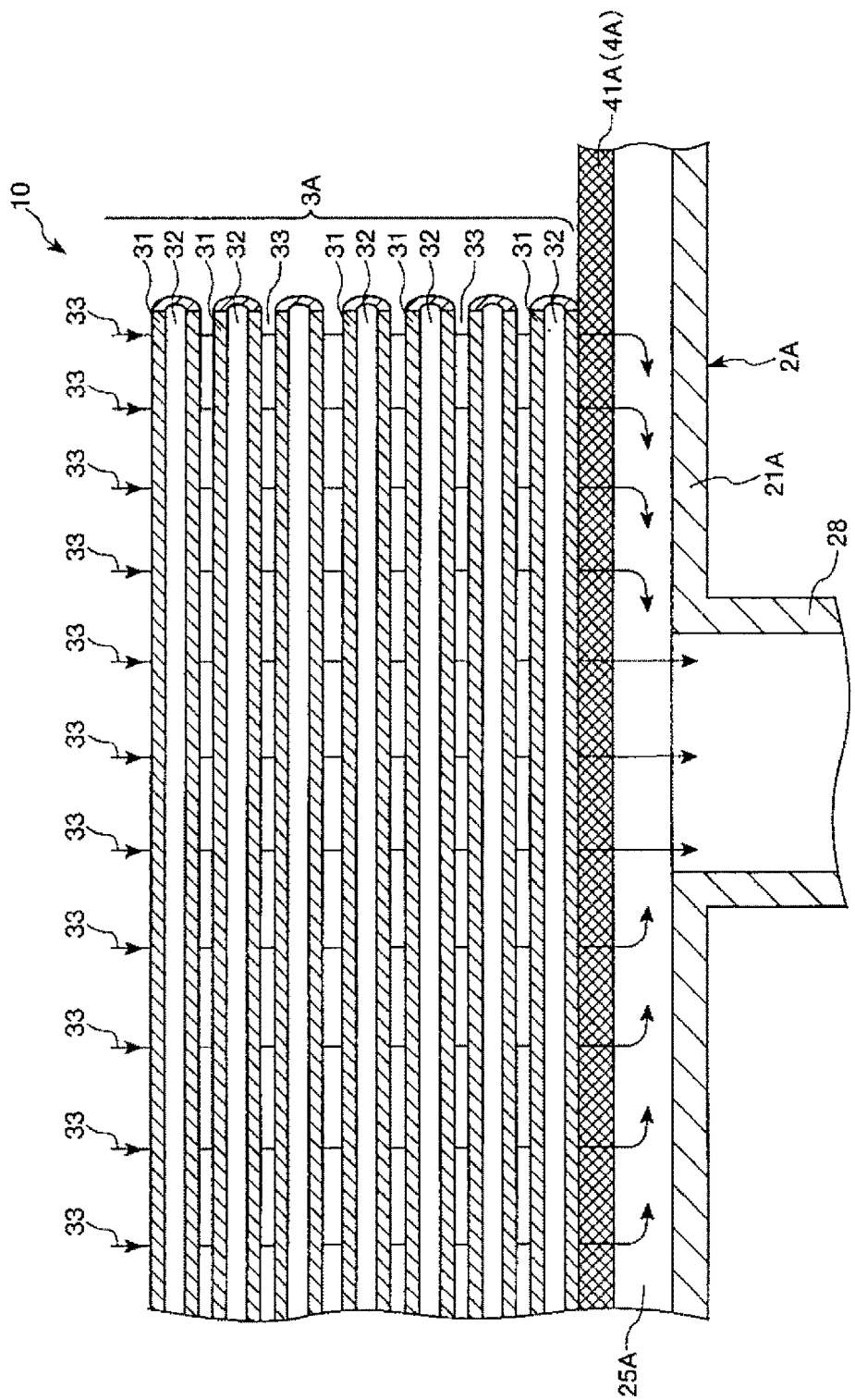
FIG. 6 is a cross-sectional view taken along the section line VI-VI in FIG. 5.

As shown in FIG. 6, each first hollow fiber membrane layer 3A is constituted with a plurality of first hollow fiber membranes 31 having a gas exchange function. In each first hollow fiber membrane layer 3A, these first hollow fiber membranes 31 are integrated. In the first laminate 30A, the plurality of first hollow fiber membrane layers 3A, which are constituted with the plurality of first hollow fiber membranes 31 having a gas exchange function, are laminated on one another. Accordingly, gas exchange can be performed in the first laminate 30A.

Furthermore, each second hollow fiber membrane layer 3A' is constituted with a plurality of second hollow fiber membranes 31' having a gas exchange function. In each second hollow fiber membrane layer 3A', these second hollow fiber membranes 31' are integrated. In the second laminate 30A', the plurality of second hollow fiber membrane layers 3A', which are constituted with the plurality of second hollow fiber membranes 31' having a gas exchange function, are laminated on one another. Accordingly, gas exchange can be performed in the second laminate 30A'.

In the Oxygenator portion 10A, the hollow fiber membrane layers for gas exchange are constituted with the first laminate 30A and the second laminate 30A'. A total number of the layers laminated on one another is not particularly limited, and is preferably, for example, 3 to 40.

Moreover, a length $L_1$ of the first hollow fiber membrane layers 3A (first laminate 30A) extending along the central axis is the same as a length $L_2$ of the second hollow fiber membrane layers 3A' (second laminate 30A') extending along the central axis. For example, $L_1$ and $L_2$ are preferably 30 mm to 250 mm, and more preferably 50 mm to 200 mm (see FIG. 8). The first hollow fiber membrane layer 3A and the second hollow fiber membrane layer 3A' satisfying the aforementioned conditions exhibit an excellent gas exchange function.

The first hollow fiber membranes 31 constituting the first hollow fiber membrane layer 3A and the second hollow fiber membranes 31' constituting the second hollow fiber membrane layer 3A' are the same as each other in terms of the size and constituting materials, except for the way they are wound. Therefore, the first hollow fiber membranes 31 will be described representatively. Note that, the way the first hollow fiber membranes 31 are wound and the way the second hollow fiber membranes 31' are wound will be described later.

Figure 10:
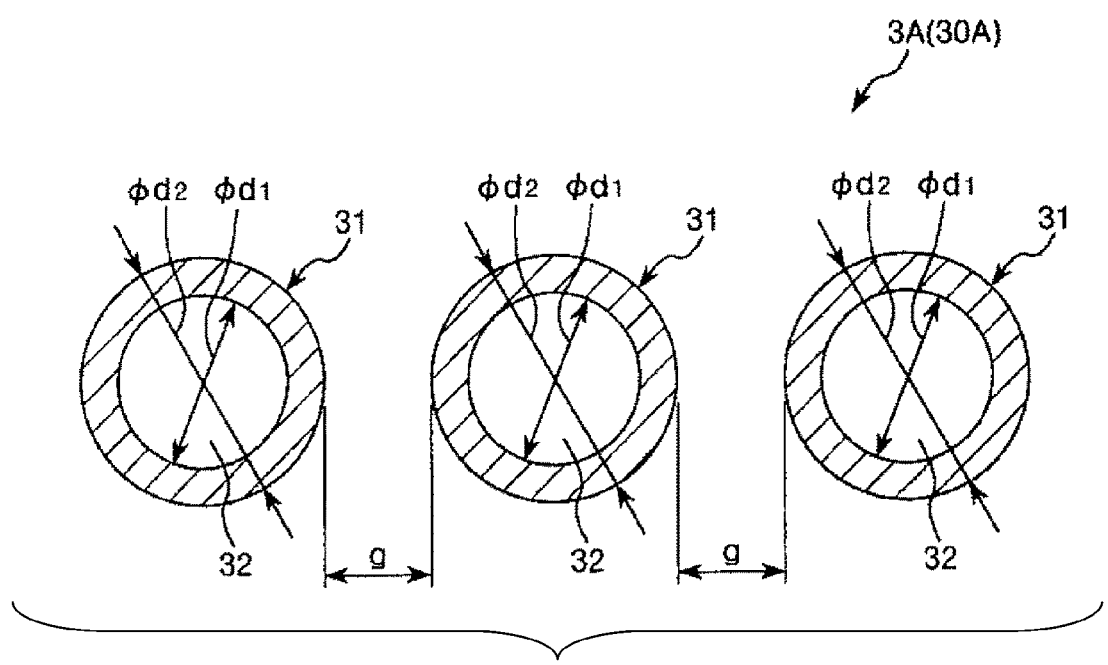
FIG. 10 is a lateral cross-sectional view of the first hollow fiber membranes in the first hollow fiber membrane layer included in the Oxygenator shown in FIG. 1.

An inner diameter $\varphi d_1$ of each of the first hollow fiber membranes 31 is preferably 50 μm to 700 μm, and more preferably 70 μm to 600 μm (see FIG. 10). An outer diameter $\varphi d_2$ of each of the first hollow fiber membranes 31 is preferably 100 μm to 900 μm, and more preferably 120 μm to 800 μm (see FIG. 10). Moreover, a ratio $d_1/d_2$ between the inner diameter $\varphi d_1$ and the outer diameter $\varphi d_2$ is preferably 0.5 to 0.9, and more preferably 0.6 to 0.8. In each of the first hollow fiber membranes 31 satisfying such conditions, strength of the membranes can be maintained, and at the same time, a degree of pressure loss occurring when gas is caused to flow in the lumen (flow path 32) of the first hollow fiber membrane 31 can be suppressed to a relatively low level. For example, if the inner diameter $\varphi d_1$ is larger than the aforementioned upper limit, the thickness of the first hollow fiber membrane 31 is reduced, and depending on other conditions, the strength of the membrane is reduced. Furthermore, if the inner diameter $\varphi d_1$ is smaller than the aforementioned lower limit, depending on other conditions, a degree of pressure loss occurring when gas flows in the lumen of the first hollow fiber membrane 31 becomes relatively high.

In addition, a gap g between the first hollow fiber membranes 31 adjacent to each other is preferably 1/10 to 1/1 of the outer diameter $\varphi d_2$ (see FIG. 10). If the gap g is within the above range, as shown in FIG. 6, a blood flow path 33, which makes it possible for blood to easily flow down toward the lower side from the upper side in the drawing, can be reliably formed in a void between the first hollow fiber membranes 31.

A method for producing such a first hollow fiber membrane 31 is not particularly limited. For example, by using a drawing process, a solid-liquid phase separation process, or the like and by appropriately regulating conditions such as a spinning speed and the amount of resin to be ejected, the first hollow fiber membrane 31 having prescribed inner diameter $\varphi d_1$ and outer diameter $\varphi d_2$ can be produced.

As a material constituting each of the first hollow fiber membranes 31, polypropylene is preferable. Moreover, it is more preferable for the first hollow fiber membrane 31 to have micropores formed in the wall portion by a drawing process or a solid-liquid phase separation process. That is, it is more preferable for the first hollow fiber membrane 31 to be constituted with porous polypropylene. If the first hollow fiber membrane 31 is formed of such a material, gas exchange between blood and the first hollow fiber membrane 31 reliably occurs.

As shown in FIG. 3, both ends of the first laminate 30A or both ends of the second laminate 30A', that is, a left end (one end) and a right end (the other end) of the first laminate 30A and the second laminate 30A' are respectively fixed to the inner surface of the cylindrical housing main body 21A by partitions 8 and 9. As a result, both ends of each of the first hollow fiber membranes 31 are in a state of being fixed to the cylindrical housing main body 21A. The partitions 8 and 9 are constituted with, for example, a potting material such as polyurethane or silicone rubber or an adhesive.

Moreover, a space between the cylindrical housing main body 21A and the heat exchange portion 10B is filled with the first laminate 30A and the second laminate 30A'. Accordingly, each of the laminates forms approximately a cylindrical shape as a whole. Consequentially, for the cylindrical housing main body 21A having the similar shape, a high packing efficiency resulting from the first laminate 30A and the second laminate 30A' is obtained (a dead space is reduced), and this makes a contribution to miniaturization and improvement of performance of the Oxygenator portion 10A.

A blood inlet space 24A that is in communication with the blood inlet port 201 is formed at the upstream side of the blood flow path 33 (i.e., at the upstream side from the heat exchange portion 10B positioned at the inner circumferential side of the Oxygenator portion 10A). The blood inlet space 24A is a blood inlet portion for the blood flowing in from the blood inlet portion 201. (see FIG. 3 and FIG. 5).

The blood inlet side space 24A is a space constituted with a first cylinder member 241 that forms a cylindrical shape and a plate piece 242 that is disposed inside the first cylinder member 241 while facing a portion of the inner circumferential portion of the first cylinder member 241. The blood flowing into the blood inlet side space 24A can flow down toward the entire blood flow path 33 through a plurality of side holes 243 formed in the first cylinder member 241.

At the downstream side of the blood flow path 33, a cylindrical void is formed between the outer circumferential surface of the filter member 41A and the inner circumferential surface of the cylindrical housing main body 21A. The void forms a blood outlet side space 25A. The blood outlet side space 25A and the blood outlet port 28 which is in communication with the blood outlet side space 25A constitute a blood outlet portion. The blood outlet portion has the blood outlet side space 25A. Accordingly, a space that allows the blood having passed through the filter member 41A to flow toward the blood outlet port 28 is secured, whereby the blood can be smoothly discharged.

Moreover, between the blood inlet side space 24A and the blood outlet side space 25A, the first hollow fiber membrane layer 3A, the filter member 41A, and the blood flow path 33 are provided.

Furthermore, at the downstream side (blood outlet portion side) of the second hollow fiber membrane layer 3A', the air bubble-removing means 4A, which captures air bubbles in the blood and removes the air bubbles from the blood, is disposed. The air bubble-removing means 4A has the filter member 41A.

The filter member 41A captures air bubbles present in the blood flowing in the blood flow path 33.

The filter member 41A is a sheet-like member (hereinafter, also simply referred to as "sheet") that forms approximately a rectangular shape. The filter member 41A is formed of the sheet wound up in the form of cylinder. Both ends of the filter member 41A are fixed by the partitions 8 and 9 respectively, and as a result, the filter member 41A is fixed to the housing 2A (see FIG. 3).

The filter member 41A is disposed such that its inner circumferential surface comes into contact with the surface of the downstream side (blood outlet portion side) of the second hollow fiber membrane layer 3A'. The filter member 41A covers approximately the entire surface of the downstream side of the second hollow fiber membrane layer 3A'. If the filter member 41A is disposed as above, an effective area of the filter member 41A can be increased, and the ability to capture air bubbles can be sufficiently demonstrated. Moreover, if the effective area of the filter member 41A is increased, even when the filter member 41A is partially clogged (for example, even when blood clots and the like adhere to the filter member 41A), it is possible to prevent overall blood flow from being impeded.

As shown in FIG. 3, at the inside of the first cap 22A, a rib 291 forming an annular shape protrudes from the inside of the first cap 22A. Moreover, a first chamber 221a is constituted with the first cap 22A, the rib 291, and the partition 8. The first chamber 221a is a gas outlet chamber from which gas flows out. The left-end opening of each of the first hollow fiber membranes 31 and the second hollow fiber membranes 31' is opened to and is in communication with the first chamber 221a.

Meanwhile, at the inside of the second cap 23A, a rib 292 forming an annular shape protrudes from the inside of the second cap 23A. Moreover, the second cap 23A, the rib 292, and the partition 9 constitute a second chamber 231a. The second chamber 231a is a gas inlet chamber into which gas flows. The right-end opening of each of the first hollow fiber membranes 31 and the second hollow fiber membranes 31' is opened to and is in communication with the second chamber 231a.

The lumen of each of the first hollow fiber membranes 31 and the lumen of each of the second hollow fiber membranes 31' constitute the flow path 32 which is a gas flow path. The gas inlet port 26 and the second chamber 231a constitute the gas inlet portion positioned at the upstream side of the flow path 32. Moreover, the gas outlet port 27 and the first chamber 221a constitute the gas outlet portion positioned at the downstream side of the flow path 32.

The heat exchange portion 10B is disposed inside the Oxygenator portion 10A. Similarly to the Oxygenator portion 10A, the heat exchange portion 10B has the first laminate 30A which is constituted with the first hollow fiber membrane layers 3A and a second laminate 30A' which is disposed at the outer circumferential side of the first laminate 30A and constituted with the second hollow fiber membrane layers 3A'. The first laminate 30A and the second laminate 30A' in the heat exchange portion 10B are the same as the first laminate 30A and the second laminate 30A' in the Oxygenator portion 10A respectively, except that the first laminate 30A and the second laminate 30A' in the heat exchange portion 10B perform heat exchange. That is, similarly to the first hollow fiber membrane layers 3A of the Oxygenator portion 10A, the first laminate 30A and the second laminate 30A', which perform heat exchange in the heat exchange portion 10B, are constituted with a plurality of the first hollow fiber membranes 31 or the second hollow fiber membranes 31'. Furthermore, in the first laminate 30A, the first hollow fiber membranes 31 are integrated, and a void (space) between the first hollow fiber membranes 31 becomes the blood flow path 33. In addition, in the second laminate 30A', the second hollow fiber membranes 31' are integrated, and a void (space) between the second hollow fiber membranes 31' becomes the blood flow path 33.

In the heat exchange portion 10B, the first laminate 30A and the second laminate 30A' constituting the heat exchange portion 10B constitute the hollow fiber membrane layers for heat exchange.

Herein, regarding the first laminate 30A and the second laminate 30A' in the heat exchange portion 10B, differences between these laminates and the first laminate 30A and the second laminate 30A' in the aforementioned Oxygenator portion 10A will be mainly described.

As shown in FIG. 3, in the heat exchange portion 10B, each of the two ends of the first laminate 30A and each of the two ends of the second laminate 30A' (that is, the left end (one end) and the right end (the other end) of each of the first laminate 30A and the second laminate 30A') are respectively fixed to the inner surface of the cylindrical housing main body 21A by the partitions 8 and 9. Moreover, the inner circumferential portion of the first laminate 30A engages a concave-convex portion 244 formed in the outer circumferential portion of the first cylinder member 241. By being engaged in this manner and being fixed by the partitions 8 and 9, the first laminate 30A is fixed to the cylindrical housing main body 21A. As a result, it is possible to prevent or inhibit occurrence of positional shift of the first laminate 30A when the Oxygenator 10 is being used.

At the inside of the first cylinder member 241, a second cylinder member 245 is disposed concentrically with the first cylinder member 241. Moreover, as shown in FIG. 3, a heat medium (for example, water) having flowed in from the heat medium inlet port 202 sequentially passes through the flow path 32 (heat medium flow path) of each of the first hollow fiber membranes 31 of the first hollow fiber membrane layer 3A positioned at the outer circumferential side of the first cylinder member 241 or the flow path 32 (heat medium flow path) of each of the second hollow fiber membranes 31' of the second hollow fiber membrane layer 3A' and the inside of the second cylinder member 245, and is then discharged out of the heat medium outlet port 203. Furthermore, when the heat medium passes through the flow path 32, heat exchange (heating or cooling) is performed between the blood, which comes into contact with the hollow fiber membrane forming the flow path 32, and the heat medium.

If the heat exchange portion 10B is disposed inside the Oxygenator portion 10A as described above, the following effects are exerted. That is, first, the Oxygenator portion 10A and the heat exchange portion 10B can be efficiently housed in a single housing 2A, and a dead space is reduced. Accordingly, gas exchange can be efficiently performed in the small Oxygenator 10. Second, the Oxygenator portion 10A and the heat exchange portion 10B are disposed close to each other. Accordingly, it is possible to allow the blood having undergone heat exchange in the heat exchange portion 10B to flow into the Oxygenator portion 10A while preventing the blood from releasing or absorbing heat as far as possible.

As materials constituting the first hollow fiber membranes 31 that constitute the heat exchange portion 10B, it is possible to use, for example, polyethylene terephthalate, polycarbonate, polyurethane, nylon, polystyrene, and vinyl chloride, in addition to those exemplified as the materials constituting the first hollow fiber membranes 31 that constitute the aforementioned Oxygenator portion 10A.

Next, blood flow in the Oxygenator 10 of the present embodiment will be described.

In the Oxygenator 10, the blood having flowed in from the blood inlet port 201 sequentially passes through the blood inlet side space 24A and the side holes 243, and flows into the heat exchange portion 10B. In the heat exchange portion 10B, the blood keeps flowing in the blood flow path 33 toward the downstream side, and in this state, the blood undergoes heat exchange (heating or cooling) by coming into contact with the surface of each of the first hollow fiber membranes 31 or the surface of each of the second hollow fiber membranes 31'. The blood having undergone heat exchange in this manner flows into the Oxygenator portion 10A.

Thereafter, in the Oxygenator portion 10A, the blood flows in the blood flow path 33 toward the downstream side. Meanwhile, the gas (oxygen-containing gas) having been supplied from the gas inlet port 26 is distributed to each flow path 32 of each of the first hollow fiber membranes 31 and second hollow fiber membranes 31' from the second chamber 231a. After flowing in the flow path 32, the gas is introduced in the first chamber 221a and discharged out of the gas outlet port 27. The blood flowing in the blood flow path 33 comes into contact with the surface of each of the first hollow fiber membranes 31 or with the surface of each of the second hollow fiber membranes 31', whereby gas exchange (addition of oxygen or removal of carbon dioxide) is performed between the blood and the gas flowing in the flow path 32.

When there are air bubbles in the blood having undergone gas exchange, these air bubbles are captured by the filter member 41A. As a result, the air bubbles are prevented from flowing out toward the downstream side of the filter member 41A.

The blood, which has undergone gas exchange and removal of air bubbles as described above, flows out of the blood outlet port 28.

As described above, the first hollow fiber membranes 31 constituting the first hollow fiber membrane layer 3A differ from the second hollow fiber membranes 31' constituting the second hollow fiber membrane layer 3A', in terms of the way they are wound (see FIG. 8 and FIG. 9). Hereinafter, the way they are wound will be described. Note that, in FIG. 8(*a*) and FIG. 9(*a*), one out of the plurality of first hollow fiber membranes 31, which constitute the first hollow fiber membrane layer 3A positioned at the outermost side of the first laminate 30A, is described representatively. Furthermore, in FIG. 8(*b*) and FIG. 9(*b*), one out of the plurality of second hollow fiber membranes 31', which constitute the second hollow fiber membrane layer 3A' positioned at the outermost side of the second laminate 30A', is described representatively.

As shown in FIG. 8(*a*) and FIG. 9(*a*), the first hollow fiber membrane layer 3A forms a cylindrical body. Moreover, the first hollow fiber membrane 31 is helically wound around a central axis 300 of the cylindrical body, in the direction indicated by the arrow in FIG. 8(*a*) and FIG. 9(*a*). The first hollow fiber membrane 31 sequentially passes through three points set on the outer circumference of the cylindrical body.

A first point (starting point) 301 is set at one site of the left-end side (one end) of the cylindrical body.

A second point (midpoint) 302 is set at one site of the right-end side (the other end) of the cylindrical body, such that the second point 302 is located in almost the same position as the first point 301 in the circumferential direction of the cylindrical body. Accordingly, provided that a line orthogonal to the central portion of the central axis 300 in the longitudinal direction is taken as a line of symmetry, the first point 301 and the second point 302 have a positional relationship in which they are symmetrical to each other relative to the line of symmetry.

A third point (endpoint) 303 is set at a site which is almost the same as the first point 301. Note that, the third point 303 may be set at one site which deviates from the first point 301 by a predetermined angle (for example, 0.5° to 15°) around the central axis 300. Herein, "almost" means that the third point 303 is not overlapped with the first point 301 and is in a position adjacent to the first point 301.

Figures 8A, 8B:
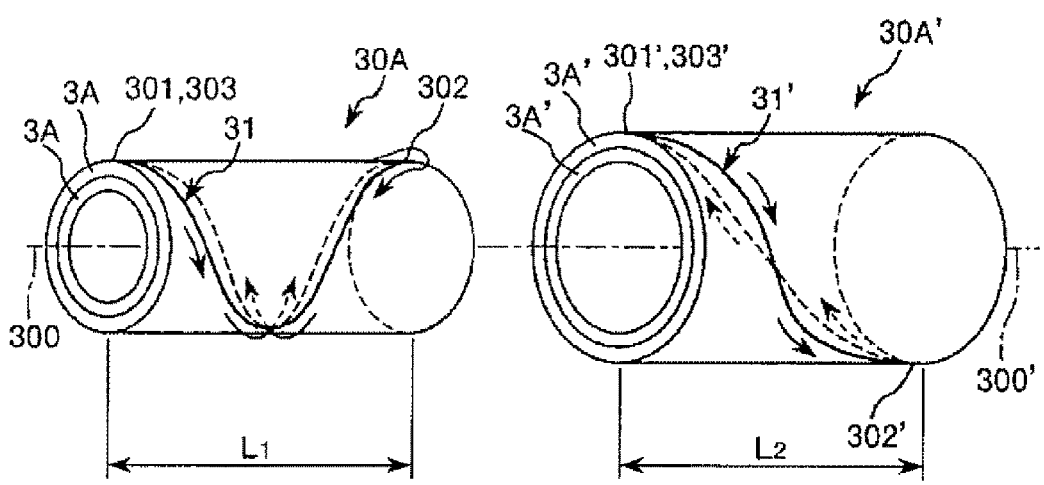
FIGS. 8(A) and 8(B) are an exploded perspective view showing the first hollow fiber membrane layer and the second hollow fiber membrane layer in FIG. 7 (FIG. 8(A) shows the first hollow fiber membrane layer, and FIG. 8(B) shows the second hollow fiber membrane layer).
Figure 9B:
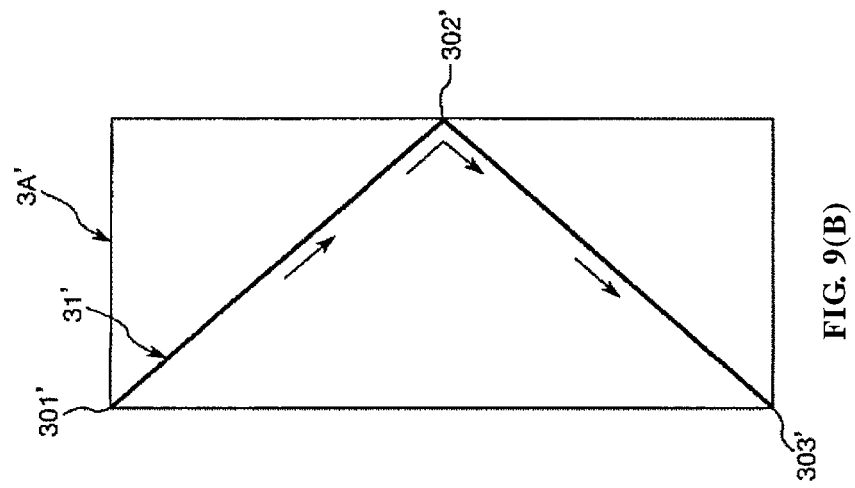
FIGS. 9(A) and 9(B) are a development view showing one first hollow fiber membrane layer and one second hollow fiber membrane layer in FIGS. 8(A) and 8(B) (FIG. 9(A) shows one first hollow fiber membrane layer, and FIG. 9(B) shows one second hollow fiber membrane layer).
Figure 9A:
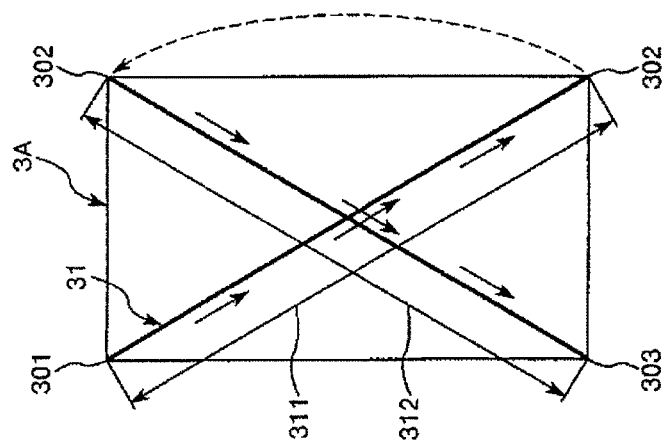

As shown in FIG. 8(a), in the outward path heading for the second point 302 (the other end) from the first point 301 (one end), the first hollow fiber membrane 31 is wound once along the circumferential direction of the cylindrical body (FIG. 9(a) shows the same constitution). The first hollow fiber membrane 31 is then folded in the second point 302. In the homeward path heading for the third point 303 (one end) from the second point 302 (the other end), the first hollow fiber membrane 31 is wound once along the same direction as the circumferential direction of the cylindrical body, as the first hollow fiber membrane 31 is wound in the outward path. In this way of winding, the first hollow fiber membrane 31 is wound twice (around the central axis 300) along the circumferential direction of the cylindrical body while it is passing through the outward path and homeward path. Moreover, in the first hollow fiber membrane 31, the middle of a portion 311 of the outward path and the middle of a portion 312 of the homeward path cross each other at one site (see FIG. 9(a)).

Note that, in the Oxygenator 10, it is preferable to provide a first engagement portion, which makes the first hollow fiber membrane 31 folded by being engaged with this portion, to the second point 302.

As shown in FIG. 8(b) and FIG. 9(b), the second hollow fiber membrane layer 3A' forms a shape of a cylindrical body (cylindrical shape). Moreover, the second hollow fiber membrane 31' is helically wound around a central axis 300' of the cylindrical body, in the direction indicated by the arrow in FIG. 8(b) and FIG. 9(b). The second hollow fiber membrane 31' sequentially passes through three points set on the outer circumference of the cylindrical body.

A first point (starting point) 301' is set at one site of the left-end side (one end) of the cylindrical body.

A second point (midpoint) 302' is set at one site of the right-end side (the other end) of the cylindrical body, such that the second point 302' is located in a position almost opposite to the first point 301' across the central axis 300'. Accordingly, provided that the central portion of the central axis 300' in the longitudinal direction is taken as a center of symmetry, the first point 301' and the second point 302' have a positional relationship in which they are practically symmetrical to each other around the center.

A third point (endpoint) 303' is set at a site which is almost the same as the first point 301'. Note that, the third point 303' may be set at one site which deviates from the first point 301' by a predetermined angle around the central axis 300'. Herein, "almost" means that the third point 303' is not overlapped with the first point 301' and is in a position adjacent to the first point 301'.

As shown in FIG. 8(b), in the outward path heading for the second point 302' (the other end) from the first point 301' (one end), the second hollow fiber membrane 31' is wound along the circumferential direction of the cylindrical body by 0.5-circumference (semi-circumference), and reaches the second point 302' from the first point 301' at the shortest distance (FIG. 9(b) shows the same constitution). Moreover, the second hollow fiber membrane 31' is folded at the second point 302'. In the homeward path heading for the third point 303' (the other end) from the second point 302' (one end), the second hollow fiber membrane 31' is also wound along the circumferential direction of the cylindrical body in the same direction as in the case of the outward path by 0.5-circumference (semi-circumference), and reaches the third point 303' from the second point 302' at the shortest distance. In this way of winding, the second hollow fiber membrane 31' is wound once (around the central axis 300') along the circumferential direction of the cylindrical body while it is passing through the outward path and homeward path.

Note that, in the Oxygenator 10, it is preferable to provide a second engagement portion, which makes the second hollow fiber membrane 31' folded by being engaged with this portion, to the second point 302'.

As described above, in the Oxygenator 10, while passing through the outward path and the homeward path, the first hollow fiber membrane 31 is wound twice along the circumferential direction of the cylindrical body. Moreover, while passing through the outward path and the homeward path, the second hollow fiber membrane 31' is wound once along the circumferential direction of the cylindrical body. That is, in the Oxygenator 10, the total number of times the second hollow fiber membrane 31' is wound is smaller than the total number of times the first hollow fiber membrane 31 is wound.

Oxygenators of the related art include an Oxygenator which has hollow fiber membrane layers consisting of a plurality of hollow fiber membranes laminated on one another and forming a shape of a cylindrical body as a whole. In each of the layers, the hollow fiber membranes travels between one end and the other end of the cylindrical body while being helically wound one by one around the central axis of the cylindrical body. Moreover, in this Oxygenator, each of the hollow fiber membranes is wound at least once around the central axis of the cylindrical body, in an outward path heading for the other end from one end of the cylindrical body. In a homeward path heading for one end from the other end, each of the hollow fiber membranes is also wound at least once around the central axis of the cylindrical body. In each of the hollow fiber membranes wound as above, a length of the layer wound once around the central axis of the cylindrical body increases toward the outer circumference of the cylindrical hollow fiber membrane layer. As a result, a length of some of the membranes from one partition to the other partition exceeds a prescribed length (certain length). In this case, in the hollow fiber membranes having a length exceeding a prescribed length, pressure loss of the gas passing through these hollow fiber membranes becomes greater than in hollow fiber membranes having a length that is within a prescribed length.

However, in the Oxygenator 10 disclosed here, the total number of times the second hollow fiber membranes 31', which constitute the second hollow fiber membrane layer 3A' positioned at the outer side (that is, the second hollow fiber membrane layer 3A' having a larger diameter between the first hollow fiber membrane layer 3A and the second hollow fiber membrane layer 3A') are wound is smaller than the total number of times the first hollow fiber membranes 31, which constitute the first hollow fiber membrane layer 3A having a smaller diameter, are wound. Accordingly, since the number of times the second hollow fiber membranes 31' are wound is reduced, the length of the second hollow fiber membranes 31' from one partition to the other partition is prevented from exceeding the prescribed length. Consequentially, it is possible to inhibit pressure loss from occurring in the second hollow fiber membranes 31' when gas passes through the inside of the second hollow fiber membranes 31'.

Moreover, in the first hollow fiber membrane layer 3A positioned at the inner side, the length of the first hollow fiber membranes 31 is controlled to be within a prescribed length. Consequentially, it is possible to inhibit pressure loss from occurring in the first hollow fiber membranes 31 when gas passes through the first hollow fiber membranes 31.

Moreover, in the heat exchange portion 10B, a length of the second hollow fiber membrane 31' of the second hollow fiber membrane layer 3A' from one partition to the other partition is prevented from exceeding a prescribed length. Consequentially, it is possible to inhibit pressure loss from occurring when a heat medium passes through the inside of the second hollow fiber membrane 31'. As a result, heat exchange can be easily and reliably performed through the second hollow fiber membrane 31'.

In order to produce the first hollow fiber membrane layer 3A by helically winding the first hollow fiber membranes 31 or to produce the second hollow fiber membrane layer 3A' by helically winding the second hollow fiber membranes 31', for example, a system including a rotary apparatus that rotates a cylindrical core, around which the hollow fiber membranes are wound, and a winder apparatus is used. At least one of the rotary apparatus and the winder apparatus moves in the axial direction of the core. Moreover, the rotary apparatus and the winder apparatus are moved relative to the axial direction of the core. In this state, the hollow fiber membranes are wound off from the winder apparatus, and the core is rotated by the rotary apparatus. In this manner, the hollow fiber membranes are helically wound around the core. Note that, the hollow fiber membranes may be wound around the core one by one, or alternatively, a plurality of the membranes may be simultaneously wound around the core.

Up to now, the medical instrument has been described in regard to the embodiments shown in the drawings, but the medical instrument disclosed here is not limited in this way. Each portion constituting the medical instrument can be replaced with a portion having any constitution that can perform the same function. Moreover, any constituent may be added to the medical instrument.

In addition, in the aforementioned embodiments, each of the first hollow fiber membrane layer and the second hollow fiber membrane layer is in the form of a laminated layer in the Oxygenator. However, the present application is not limited in this way, and for example, at least one of the first hollow fiber membrane layer and the second hollow fiber membrane layer may be a single layer.

Moreover, in the aforementioned embodiments, each of the hollow fiber membranes constituting each of the hollow fiber membrane layers of the Oxygenator portion is the same as each of the hollow fiber membranes constituting each of the hollow fiber membrane layers of the heat exchange portion. However, the hollow fiber membranes are not limited to this configuration, and for example, one (the former) hollow fiber membrane may be finer than the other (the later) hollow fiber membrane, or alternatively, both the hollow fiber membranes may be constituted with different materials.

Furthermore, inside the heat exchange portion, a hollow fiber membrane layer having the same function as each of the hollow fiber membrane layers of the Oxygenator portion, that is, a hollow fiber membrane layer having a gas exchange function may be disposed.

In addition, in the aforementioned embodiments, the heat exchange portion includes hollow fiber membrane layers having a heat exchange function. However, the heat exchange portion may include a so-called bellows-type heat exchanger. The exchanger can be constituted with metal materials such as stainless steel and aluminum or resin materials such as polyethylene, polyethylene terephthalate, polycarbonate, polyurethane, and nylon.

Moreover, in the aforementioned embodiments, in each of the outward path heading for the second point from the first point and the homeward path heading for the third point from the second point, the first hollow fiber membrane is wound once along the circumferential direction of the cylindrical body. However, the medical instrument disclosed here is not so limited, and the first hollow fiber membrane may be wound twice or more times.

Furthermore, in each of one first hollow fiber membrane and one second hollow fiber membrane, a series of pathways having an outward path and a homeward path may be repeated plural times. If the pathways are repeated plural times, each of the first hollow fiber membranes or each of the second hollow fiber membranes can be continuously wound, and accordingly, the production efficiency of the first hollow fiber membrane layer or the second hollow fiber membrane layer is improved.

The medical instrument includes at least one first hollow fiber membrane layer which has a plurality of first hollow fiber membranes, obtained by integrating the plurality of first hollow fiber membranes, and forms a shape of a cylindrical body as a whole, and at least one second hollow fiber membrane layer which is disposed at the outer circumferential side of the first hollow fiber membrane layer in a state of being concentric with the first hollow fiber membrane layer, has a plurality of second hollow fiber membranes, is obtained by integrating the plurality of second hollow fiber membranes, and forms a shape of a cylindrical body as a whole, in which each of the first hollow fiber membranes and the second hollow fiber membranes is wound around the central axis of the cylindrical body, and a number of times the second hollow fiber membranes are wound is smaller than a number of times the first hollow fiber membranes are wound. Accordingly, each of the first hollow fiber membranes and the second hollow fiber membranes is prevented from exceeding a certain length.

The detailed description above describes embodiments of a medical instrument and a method for producing a medical instrument representing examples of the medical instrument and method of the present invention. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical instrument comprising:
    at least one first hollow fiber membrane layer comprised of a plurality of integrated first hollow fiber membranes, the first hollow fiber membrane layer being configured as a cylindrically-shaped body, and possessing an outer circumferential side and a central axis extending along an axial length of the cylindrically-shaped body of the first hollow fiber membrane;
    and at least one second hollow fiber membrane layer disposed at the outer circumferential side of the first hollow fiber membrane layer concentric with the first hollow fiber membrane layer, the second hollow fiber membrane layer being comprised of a plurality of integrated second hollow fiber membranes, the second hollow fiber membrane layer being configured as a cylindrical-shaped body, wherein each of the first hollow fiber membranes and each of the second hollow fiber membranes is wound around the central axis of the cylindrical body;

wherein each of the first hollow fiber membranes sequentially begins at a starting point set at one site at one end of the cylindrically-shaped body, continues to a midpoint, and ends at an endpoint set at one site in the same position as the starting point or in a position deviating from the starting point around the central axis;

wherein each of the first hollow fiber membranes is wound in a first winding pattern from the starting point to the endpoint, the first winding pattern defined by the first hollow fiber membranes being wound at least once in the circumferential direction around the central axis of the cylindrical body in an outward path from the starting point towards the midpoint, and being wound by the same number of turns in a same direction as in the case of the outward path in a homeward path from the midpoint towards the endpoint;

wherein each of the second hollow fiber membranes sequentially begins at a starting point set at one site at an end of the cylindrically-shaped body, continues to a midpoint, and reaches an endpoint set at one site at the same position as the starting point or in a position deviating from the starting point around the central axis;

wherein each of the second hollow fiber membranes is wound in a second winding pattern from the starting point to the endpoint, the second winding pattern being defined by each of the second hollow fiber membranes being wound by one half a circumference in the circumferential direction around the central axis of the cylindrical body in an outward path from the starting point towards the midpoint, and being wound by a same number of turns in a same direction as in the case of the outward path in a homeward path from the midpoint towards the endpoint; and whereby the first winding pattern of the first hollow fiber members around the central axis of the cylindrical body is different from the second winding pattern of the second hollow fiber membranes around the central axis of the cylindrical body.

2. The medical instrument according to claim 1,
wherein the cylindrically-shaped body of the first hollow fiber membrane layer possesses one end and an other end,
wherein in the first winding pattern each of the first hollow fiber membranes extends along an outward path extending from the one end to the other end and a homeward path extending from the other end to the one end, each of the first hollow fiber membranes extending helically at least once around the central axis in the outward path, and extending helically at least once around the central axis in the homeward path.

3. The medical instrument according to claim 1,
wherein the midpoint is set at one site at an opposite end of the cylindrically-shaped body such that the midpoint is in an almost same position as the starting point in the circumferential direction of the cylindrical body, and
wherein in the first winding pattern each of the first hollow fiber membranes is wound at least once in the circumferential direction in the outward path heading for the midpoint from the starting point, and is wound at least once in the circumferential direction of the cylindrical body in the same direction as in the case of the outward path in the homeward path heading for the endpoint from the midpoint.

4. The medical instrument according to claim 2,
wherein in each of the first hollow fiber membranes, a series of pathways having the outward path and the homeward path are repeated plural times.

5. The medical instrument according to claim 1,
wherein the cylindrically-shaped body of the second hollow fiber membrane layer possesses one end and an other end, wherein in the second winding pattern each of the second hollow fiber membranes extends along the outward path extending from the one end to the other end and extends along the homeward path extending from the other end to the one end, and is wound once around the central axis while extending along the outward path and the homeward path.

6. The medical instrument according to claim 5,
wherein in each of the second hollow fiber membranes, a series of pathways having the outward path and the homeward path are repeated plural times.

7. The medical instrument according to claim 1,
wherein in the second winding pattern the midpoint is set at one site at an opposite end of the cylindrically-shaped body such that the midpoint is in a position opposite to the starting point across the central axis, and each of the second hollow fiber membranes reaches the midpoint from the starting point at a shortest distance while being wound in the circumferential direction of the cylindrically-shaped body in the outward path heading for the midpoint from the starting point, and each of the second hollow fiber membranes reaches the endpoint from the midpoint at a shortest distance while being extending helically in the circumferential direction of the cylindrical body in the same direction as in the case of the outward path in the homeward path heading for the endpoint from the midpoint.

8. The medical instrument according to claim 1,
wherein an inner diameter of the first hollow fiber membranes is the same as an inner diameter of the second hollow fiber membranes.

9. The medical instrument according to claim 1,
wherein an outer diameter of the first hollow fiber membranes is the same as an outer diameter of the second hollow fiber membranes.

10. The medical instrument according to claim 1,
wherein a gap between the first hollow fiber membranes adjacent to each other is the same as a gap between the second hollow fiber membranes adjacent to each other.

11. The medical instrument according to claim 1,
wherein materials constituting the first hollow fiber membranes are the same as materials constituting the second hollow fiber membranes.

12. The medical instrument according to claim 1,
wherein a length of the first hollow fiber membrane layer extending along the central axis direction is the same as a length of the second hollow fiber membrane layer extending along the central axis direction.

13. The medical instrument according to claim 1, comprising:
a plurality of the first hollow fiber membrane layers; and
a plurality of the second hollow fiber membrane layers,
wherein a first laminate is constituted with the plurality of the first hollow fiber membrane layers, and a second laminate is constituted with the plurality of the second hollow fiber membrane layers.

14. The medical instrument according to claim 1, wherein each of the first hollow membrane layer and the second hollow membrane layer has a function of performing at least one of a gas exchange and a heat exchange.

15. The medical instrument according to claim 14, wherein the medical instrument is an Oxygenator.

16. The medical instrument according to claim 1, wherein the at least one second hollow fiber membrane layer disposed at the outer circumferential side of the first hollow fiber membrane layer surrounds the first hollow fiber membrane layer.

17. A method of producing a medical instrument, the medical instrument including a first hollow fiber membrane layer comprised of a plurality of integrated first hollow fiber membranes, and a second hollow fiber membrane layer comprised of a plurality of integrated second hollow fiber membranes, the method comprising:

helically winding each of the first hollow fiber membranes in a first winding pattern around a central axis of a cylindrical body from a starting point to an endpoint, the first winding pattern defined by the first hollow fiber membranes being wound at least once in a circumferential direction around the central axis of the cylindrical body in an outward path from the starting point towards a midpoint, and being wound by the same number of turns in a same direction as in the case of the outward path in a homeward path from the midpoint towards the endpoint such that each of the first hollow fiber membranes extends helically about the central axis to form the first hollow fiber membrane layer;

helically winding each of the second hollow fiber membranes in a second winding pattern around the central axis of the cylindrical body, in surrounding relation to the first hollow fiber membrane layer, from the starting point to the endpoint, the second winding pattern being defined by each of the second hollow fiber membranes being wound by one half a circumference in the circumferential direction around the central axis of the cylindrical body in an outward path from the starting point towards the midpoint, and being wound by a same number of turns in a same direction as in the case of the outward path in a homeward path from the midpoint towards the endpoint such that each of the second hollow fiber membranes extends helically about the central axis to form the second hollow fiber membrane layer; and wherein the first winding pattern is different than the second winding pattern.

* * * * *